(12) United States Patent
Losego et al.

(10) Patent No.: US 10,364,491 B2
(45) Date of Patent: Jul. 30, 2019

(54) PROCESS TO CHEMICALLY MODIFY POLYMERIC MATERIALS BY STATIC, LOW-PRESSURE INFILTRATION OF REACTIVE GASEOUS MOLECULES

(71) Applicant: Georgia Tech Research Corporation, Atlanta, GA (US)

(72) Inventors: Mark D. Losego, Atlanta, GA (US); Collen Z. Leng, Atlanta, GA (US); Brandon Deane Piercy, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 15/802,182

(22) Filed: Nov. 2, 2017

(65) Prior Publication Data

US 2018/0127870 A1  May 10, 2018

Related U.S. Application Data

(60) Provisional application No. 62/416,279, filed on Nov. 2, 2016.

(51) Int. Cl.
*C23C 16/04* (2006.01)
*C08J 3/20* (2006.01)
(Continued)

(52) U.S. Cl.
CPC ............ *C23C 16/045* (2013.01); *A01N 25/10* (2013.01); *A01N 55/02* (2013.01); *A61L 15/20* (2013.01); *A61L 15/26* (2013.01); *C08B 15/00* (2013.01); *C08B 15/05* (2013.01); *C08F 120/14* (2013.01); *C08G 63/916* (2013.01); *C08G 64/42* (2013.01); *C08J 3/203* (2013.01); *C08J 3/28* (2013.01); *C08K 3/22* (2013.01); *C08K 5/56* (2013.01); *C23C 16/52* (2013.01); *A61L 2300/404* (2013.01); *C08J 2301/02* (2013.01); *C08J 2333/12* (2013.01); *C08J 2367/02* (2013.01);
(Continued)

(58) Field of Classification Search
CPC ........ C23C 16/045; C23C 16/08; C23C 16/18
See application file for complete search history.

(56) References Cited

U.S. PATENT DOCUMENTS 3,871,912 A * 3/1975 Dierssen ........... H01L 21/02406
117/109
4,379,020 A * 4/1983 Glaeser .................. C30B 1/023
117/8
(Continued)

FOREIGN PATENT DOCUMENTS

| EP | 3056477 | 8/2016 |
|---|---|---|
| WO | 199931958 | 7/1999 |
| WO | 2017095699 | 6/2017 |

OTHER PUBLICATIONS

Delhaes, P., et al., "Chemical vapor deposition and infiltration processes of carbon materials". Carbon 40 (2002) 641-657.*
(Continued)

*Primary Examiner* — Bret P Chen
(74) *Attorney, Agent, or Firm* — Troutman Sanders LLP; Ryan A. Schneider

(57) ABSTRACT

Disclosed herein are methods for diffusing precursors into polymer substrates, including methods of chemically modifying polymeric materials by static, low-pressure infiltration of reactive gaseous molecules.

14 Claims, 5 Drawing Sheets

(51) Int. Cl.

| | |
|---|---|
| C08G 63/91 | (2006.01) |
| C08G 64/42 | (2006.01) |
| C08B 15/05 | (2006.01) |
| C08F 120/14 | (2006.01) |
| C08K 5/56 | (2006.01) |
| C08K 3/22 | (2006.01) |
| A01N 55/02 | (2006.01) |
| A01N 25/10 | (2006.01) |
| A61L 15/26 | (2006.01) |
| A61L 15/20 | (2006.01) |
| C08J 3/28 | (2006.01) |
| C23C 16/52 | (2006.01) |
| C08B 15/00 | (2006.01) |

(52) U.S. Cl.
CPC ... *C08J 2369/00* (2013.01); *C08K 2003/2241* (2013.01); *C08K 2003/2296* (2013.01)

(56) References Cited

U.S. PATENT DOCUMENTS

| | | | |
|---|---|---|---|
| 5,904,957 | A | 5/1999 | Christin et al. |
| 6,730,802 | B2 * | 5/2004 | Shen ................ C07F 7/0896 427/96.2 |
| 8,236,379 | B2 | 8/2012 | Boris et al. |
| 9,277,998 | B2 | 3/2016 | Vargas et al. |
| 9,376,750 | B2 | 6/2016 | George et al. |
| 2005/0067346 | A1 * | 3/2005 | Noack ................ B01D 53/228 210/503 |
| 2008/0119098 | A1 | 5/2008 | Palley et al. |
| 2009/0137043 | A1 | 5/2009 | Parsons et al. |
| 2010/0204443 | A1 * | 8/2010 | Gazit ................ C23C 14/12 530/300 |
| 2012/0321779 | A1 * | 12/2012 | Vargas ................ C23C 16/045 427/2.26 |
| 2017/0352869 | A1 * | 12/2017 | Zhamu ................ H01M 4/1393 |

OTHER PUBLICATIONS

Tao, Yuqiang, et al., "Preparation of Nickel Ferrite-Copper Composite by Pressureless Infiltration". J. Am. Ceram. Soc., 95[12] 3739-3742 (2012).*
Zhu, Yaochan, et al., "Numerical Modeling Chemical Vapor Infiltration of SiC Composites". Journal of Chemistry, vol. 2013, Article ID 836187, 11 pages.*
Xu, Yongdong, et al., "Effects of chemical vapor infiltration atmosphere on the mechanical properties and microstructures of carbon fibers". Journal of the European Ceramic Society 21 (2001) 809-816.*
Akyildiz, et al, "Temperature and Exposure Dependence of Hybrid Organic-Inorganic Layer Formation by Sequential Vapor Infiltration into Polymer Fibers," Langmuir 2012, vol. 28 pp. 15697-15704.
Akyildiz, et al., "Formation of Novel Photoluminescent Hybrid Materials by Sequential Vapor Infiltration into Polyethylene Terephthalate Fibers," Dec. 14, 2014 vol. 29, No. 23 pp. 2817-2826.
Cianci, et al., "Trimethylaluminum Diffusion in PMMA Thin Films During Sequential Infiltration Synthesis: in Situ Dynamic Spectroscopic Ellipsometric Investigation," Adv. Mater. Interfaces 2018, 1801016.
Dandley, et al., "Wafer-Scale Selective-Area Deposition of Nanoscale Metal Oxide Features Using Vapor Saturation into Patterned Poly(methyl methacrylate) Templates," 2016 Adv. Mater. Interfaces pp. 1-9.
Dandley, et al., "Temperature-Dependent Reaction Between Trimethylaluminum and poly(methyl methacrylate) During Sequential Vapor Infiltration: Experimental and ab initio Analysis," 2014 J. Mater. Chem. C vol. 2 pp. 9416-9424.
Dusoe, et al., "Ultrahigh Elastic Strain Energy Storage in Metal-Oxide-Infiltrated Patterned Hybrid Polymer Nanocomposites," Nano Lett. 2017, 17, 7416-7423.
Ferguson, et al., "Atomic Layer Deposition of Al2O3 Films on Polyethylene Particles," 2004 Chem. Mater. pp. 5602-5609.
Gong, et al., "Hydrophilic Mechanical Buffer Layers and Stable Hydrophilic Finishes on Polydimethylsiloxane Using Combined Sequential Vapor Infiltration and Atomic/Molecular Layer Deposition," 2012 Journal of Vacuum Science Technology A pp. 156-1-156-5.
Gong and Parsons, "Quantitative in situ Infrared Analysis of Reactions Between Trimethylaluminum and Polymers During Al2O3 Atomic Layer Deposition," 2012 J. Mater. Chem. vol. 22 15672-15682.
During Al2Oe Atomic Layer Deposition, J. Mater. Chem., 2012, 22, 15672.
Gong, et al., "Sequential Vapor Infiltration of Metal Oxides into Sacrificial Polyester Fibers: Shape Replication and Controlled Porosity of Microporous/Mesoporous Oxide Monoliths," 2011 Chem. Mater. vol. 23, pp. 3476-3485.
Gregorczyk & Knez, "Hybrid Nanomaterials Through Molecular and Atomic Layer Deposition: top Down, Bottom Up, and In-Between Approaches to New Materials," 2016, Progress in Materials Science pp. 1-37.
Gregorcyzk, et al, "Tuning the Tensile Strength of Cellulose Through Vapor-Phase Metalation," 2015 Chem Mater. vol. 27 pp. 181-188.
Hyde, et al., "Atomic Layer Deposition and Abrupt Wetting Transitions on Nonwoven Polypropylene and Woven Cotton Fabrics," 2010 Langmuir, 26(4) pp. 2550-2558.
Jur, et al, "Temperature-Dependent Subsurface Growth During Atomic Layer Deposition on Polypropylene and Cellulose Fibers," Langmuir 2010, 26(11) 8239-8244.
Knez, Mato, "Diffusion Phenomenal in Atomic Layer Deposition," 2012 Semicond. Sci. Technol. vol. 27 pp. 1-8.
Lee, et al., "Improved Mechanical Stability of Dried Collagen Membrane After Metal Infiltration," 2010 ACS Applied Materials & Interfaces vol. 2 No. 8 pp. 2436-2441.
Lee, et al., "In Situ Raman Spectroscopic Study of Al-Infiltrated Spider Dragline Silk Under Tensile Deformation," 2014 ACS Appl. Mater. Interfaces, vol. 6, pp. 16827-16834.
Lee, et al., "Greatly Increased Toughness of Infiltrated Spider Silk," Science, Apr. 24, 2009, vol. 324, pp. 488-492.
Leng and Losego, "Vapor Phase Infiltration (VPI) for Transforming Polymers into Organic-Inorganic Hybrid Materials: A Critical Review of Current Progress and Future Challenges," Mater. Horiz., 2017, 4, 747-771.
Leng and Losego, "A Physiochemical Processing Kinetics Model for the Vapor Phase Infiltration of Polymers: Measuring the Energetics of Precursor-Polymer Sorption, Diffusion, and Reaction," Phys. Chem. Chem. Phys., 2018, 20, 21506-21514.
McClure, et al., 'Effect of Al2O3 ALD Coating and Vapor Infusion on the Bulk Mechanical Response of Elastic and Viscoelastic Polymers, 2015, Surface & Coatings Technology vol. 261, pp. 411-417.
Obuchovsky, et al., "Mechanism of Metal Oxide Deposition from Atomic Layer Deposition Inside Nonreactive Polymer Matrices: Effects of Polymer Crystallinity and Temperature," 2016 Chem. Mater. vol. 28 pp. 2668-2676.
Obuchovsky, et al., "Atomic Layer Deposition of Zing Oxide Onto and Into P3HT for Hybrid Photovoltaics," 2014 J. Mater. Chem. vol. 2 pp. 8903-8910.
Obuchovsky, et al., "Harnessing ALD to Directly Map the Morphology of Organic Photovoltaic Buk Heterojunctions," 2015 Solar Energy Materials & Colar Cells vol. 143 pp. 280-283.
Oldham, et al., "Encapsulation and chemical Resistance for Electrospun Nylon Nanofibers Coated Using Integrated Atomic and Molecular Layer Deposition," 2011 Journal of the Electrochemical Society vol. 158 No. 9 pp. D549-D556.
Padbury and Jur, Temperature-Dependent Infiltration of Polymers During Sequential Exposures to Trimethylaluminum,: Langmuir 2014, 30, 9228-9238.
Padbury and Jur, "Comparison of Precursor Infiltration into Polymer Thin Films via Atomic Layer Deposition and Sequential Vapor Infiltration Using in-situ Quartz Crystal Microgravimetry," J. Vac. Sci. & Technol. Jul./Aug. 2014, 32, 041602-1-041602-7.

(56) References Cited

OTHER PUBLICATIONS

Padbury & Jur, "Systematic Study of Trimethyl Aluminum Infiltration in Polyethylene Terephthalate and Its Effect on the Mechanical Properties of Polyethylene Terephthalate Fibers," 2014 J. Vac. Sci. technol. 33(1) pp. 1-9.

Padbury and Jur, "Effect of Polymer Microstructure on the Nucleation Behavior of Alumina Via Atomic Layer Deposition," 2014 J. Phys. Chem. C vol. 118, pp. 18805-18813.

Parsons, et al., "Mechanisms and Reactions During Atomic Layer Deposition on Polymers," Coordination Chemistry Reviews 2013, 257, 3323-3331.

Peng, et al., "Nanoscopic Patterned Materials with Tunable Dimensions via Atomic Layer Deposition on Block Copolymers," 2010 Adv. Mater. vol. 22 pp. 5129-5133.

Peng, et al., "A Route to Nanoscopic Materials via Sequential Infiltration Synthesis on Block Copolymer Templates," 2011, ACSnano, vol. 5., No. 6., pp. 4600-4606.

Ramanathan, et al., "Emerging Trends in Metal-Containing Block Copolymers: Synthesis, Self-Assembly, and Nanomanufacturing Applications," Mar. 21, 2013, vol. 1 No. 11 pp. 2080-2091.

Segal-Peretz, et al., "Characterizing the Three-Dimensional Structure of Block Copolymers via Sequential Infiltration Synthesis and Scanning transmission Electron Tomography," 2015 ACSnano.org vol. 9 No. 5, pp. 5333-5347.

Sinha, et al., "Transport Behavior of Atomic Layer Deposition Precursors Through Polymer Masking Layers: Influence on Area Selective Atomic Layer Deposition," J. Vac. Sci. Technol. Sep./Oct. 2007, 25(5), 1721-1728.

Sinha, et al., "Area Selective Atomic Layer Deposition of Titanium Dioxide: Effect of Precursor Chemistry," Nov./Dec. 2006, J. Vac. Sci. Technol. 24(6) pp. 2523-2532.

Spagnola, et al. "Surface and Sub-Surface Reactions During Low Temperature Aluminium Oxide Atomic Layer Deposition on Fiber-Forming Polymers," 2010 J. Mater. Chem vol. 20 pp. 4213-4222.

Tseng, et al., "Enhanced Block Copolymer Lithography Using Sequential Infiltration Synthesis," 2011 American Chemical Society vol. 115 pp. 17725-17729.

Tseng, et al., "Etch Properties of Resists Modified by Sequential Infiltration Synthesis," 2011, J. Vac. Sci. Technol. 29 (6) pp. 1-4.

Tseng, et al., "Enhanced Polymeric Lithography Resists via Sequential Infiltration Synthesis," 2011 J. Mater. Chem., vol. 21 pp. 11722-11725.

Wang, et al., "Efficient and Controllable Vapor to Solid Doping of the Polythiophene P3HT by Low Temperature Vapor Phase Infiltration," J. Mater. Chem. C, 2017, 5 2686-2694.

Zhang, et al., "Chemical Infiltration During atomic Layer Deposition: Metalation of Porphyrins and Model Substrates," 2009 Agnew. Chem. Int. Ed. vol. 48 pp. 4982-4985.

Directed Inorganic Modification of bi-Component Polymer Fibers by Selective Vapor Reaction and Atomic Layer Deposition, 2012 Polymer, vol. 53, pp. 4631-4536.

\* cited by examiner

PROCESS TO CHEMICALLY MODIFY POLYMERIC MATERIALS BY STATIC, LOW-PRESSURE INFILTRATION OF REACTIVE GASEOUS MOLECULES

CROSS-REFERENCE TO RELATED APPLICATIONS

This application claims the benefit of U.S. Provisional Patent Application Ser. No. 62/416,279, filed Nov. 2, 2016, entitled "A Process To Chemically Modify Polymeric Materials By Static, Low-Pressure Infiltration Of Reactive Gaseous Molecules," the entire contents and substance of which are hereby incorporated by reference as if fully set forth below.

TECHNICAL FIELD

The present disclosure pertains to a gas phase processing scheme for producing organic-inorganic hybrid materials.

BACKGROUND

Polymeric materials can be chemically modified for a variety of reasons, but known methods can be costly, complex, and/or environmentally unfriendly. Improved methods for chemically modifying polymeric materials are desirable.

SUMMARY

Methods of chemically modifying polymeric materials by static, low-pressure infiltration of reactive gaseous molecules are disclosed herein. Systems for chemically modifying polymeric materials by static, low-pressure infiltration of reactive gaseous molecules, are also disclosed.

In certain aspects of the disclosure, the method of operating a chemical vapor infiltration chamber includes the steps of loading a substrate into a vacuum chamber of a chemical vapor infiltration apparatus, the vacuum chamber having a first end and a second end with a high vacuum pump located proximate said second end; pumping the vacuum chamber to a pressure of from 8 mTorr to 12 mTorr with the vacuum pump; dosing the substrate with a precursor by allowing the precursor to flow inside the chamber; creating a static precursor atmosphere inside the chamber; allowing the substrate to rest in the static precursor atmosphere from 30 seconds to 1 day to form a chemically modified substrate; and extracting the chemically modified substrate from the reaction chamber.

In certain aspects of the disclosure, the method of operating a chemical vapor infiltration apparatus, the method comprising the steps of loading a polymeric material into a vacuum chamber of the chemical vapor infiltration apparatus, the vacuum chamber having a first end and a second end with a high vacuum pump located proximate said second end; pumping the vacuum chamber to a pressure of from 8 mTorr to 12 mTorr with said vacuum pump; dosing the polymeric material with a metalorganic precursor by allowing the precursor to flow inside the chamber; creating a static precursor atmosphere inside the chamber; allowing the substrate to rest in the static precursor atmosphere from 30 seconds to 1 day to form a chemically modified polymeric material; and extracting a chemically modified polymeric material from the chamber.

The present disclosure also provides a system for chemically modifying polymeric materials by static, low-pressure infiltration of reactive gaseous molecules, comprising a vacuum chamber; the vacuum chamber attached to a vacuum pump for controlling pressure inside the vacuum chamber; a substrate loaded inside the vacuum chamber; and a precursor holder positioned to dose precursors directly into the vacuum chamber.

DETAILED DESCRIPTION

Figure 1:
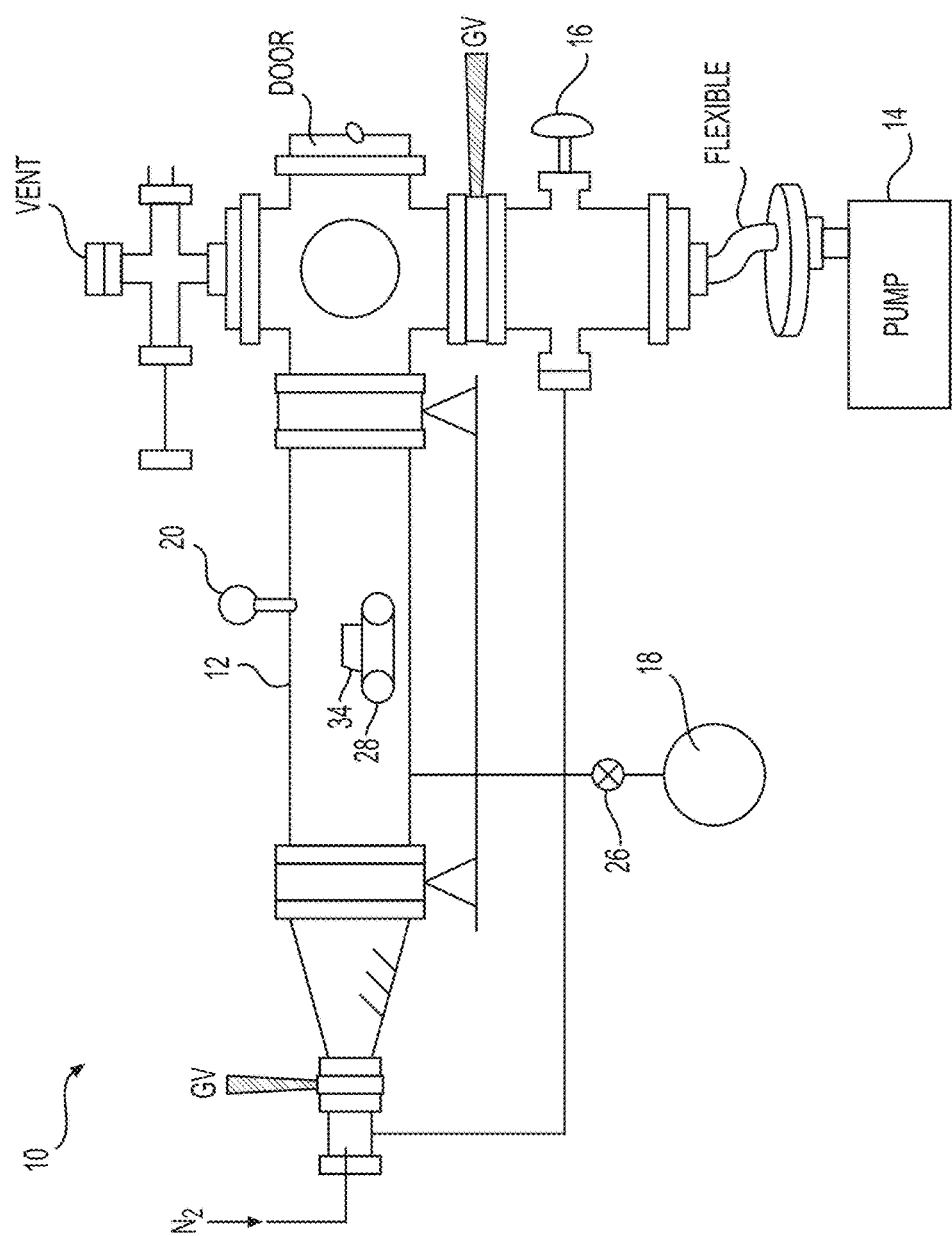
FIG. 1 illustrates a VPI reaction chamber, in accordance with an embodiment of the present disclosure.

Vapor phase infiltration (VPI) is a technique that can be used for chemically modifying a variety of polymeric materials using, for instance, low-pressure, highly reactive gases. These chemical modifications can produce a variety of effects including hydrophobicity, antibacterial or bacteriostatic behavior, solvent resistance, dimensional changes, and/or energy beam resistance. The precise effects can depend on both the polymeric material, the reactant gases used, and the processing conditions.

Atomic layer deposition (ALD) can be used to modify polymers. ALD can be a time- or space-separated sequential deposition of alternating co-reactants. In ALD, thin, conformal metal oxide films can be deposited on polymeric substrates. However, ALD can depend on continuous, dense film deposits on the surface of the polymer substrate. This approach can require repeated deposition cycling to build up a sufficient oxide coating.

Solution deposition can refer to the settling of particles from a solution or suspension onto a pre-existing surface, resulting in the growth of a new phase. However, solution deposition can be limited by surface tension and viscosity. As fibers and other materials reach smaller sizes, it can become difficult for liquids to effectively penetrate these substrates. Solvents must also be selected for the particular substrate or polymer at hand, limiting which processes can be used with each polymer type. In many solution processing techniques, there can be also substantial waste and environmental hazards associated with any required solvents.

Unlike solution deposition, VPI does not use solvents. So it is broadly compatible with many substrate types. Moreover, any unreacted precursor in the VPI process can be vented to the atmosphere, where it immediately reacts with water molecules and forms a nontoxic metal oxide, which can be recycled. Or, using a cold trap, gaseous precursors can be condensed out of the carrier gas or byproduct gas stream and then be recycled for use. As a gas phase process, it is also not limited by surface tension or viscosity, meaning that reaction, and the resulting modification, can occur across the entire surface of the polymer substrate, regardless of structure.

Nanostructured surfaces are another approach used to engineer properties on materials. However, they are limited to specific, typically planar, substrates, and tend to lose their properties through mechanical abrasion or chemical attack over time. VPI-modified materials are transformed throughout their bulk, and so behave as a homogeneous material. There is no reliance on the physical structure of the material; so changes to the structure do not impact the material performance.

There is a long-felt need for a system and method that would minimize the complexities of gas handling in processes like ALD, and reduce the associated cost and involvedness of the associated equipment. VPI achieves these ends, reducing gas handling costs by at least 50%, for example. The VPI environment is more tolerant of minor oxygen or water leaks into the chamber, as any impurities are simply precipitated out as powder. Further, VPI scales to large volumes much more efficiently than ALD. In ALD, increasing processing volume introduces significant challenges to the fluid dynamics in the chamber, with unpredictable effects on the quality of the film deposition. As such, it is often better to keep chambers relatively small and focus on planar substrates.

The disclosed VPI technique has no requirement for repeated cycling, such as with ALD, and imparts its properties by direct chemical interaction with the polymer substrate. Moreover, with VPI, there is no worry about vapor homogeneity, as the atmosphere is static. This means that VPI is able to process bulk materials that are economically inaccessible to ALD. Significantly faster process times are also observed, in the range of a few minutes for VPI versus several hours for ALD. Diffusion control in VPI also allows the development of diffusion-linked properties, while ALD limits the time that the substrate is exposed to the precursor, introducing a competition between diffusion into the bulk and deposition of an oxide layer.

Herein, it is demonstrated that these chemical modifications can be achieved with VPI by holding substrates in a static atmosphere environment for extended times instead of requiring sequential deposition processing used by ALD.

This disclosure both obviates the need for a costly and complex gas handling system and accelerates processing time relative to ALD, and other similar methods.

Although some embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways.

Disclosed are various vapor phase infiltration reactor systems and methods. The presently disclosed vapor phase infiltration reactor systems and methods can have the added benefit of yielding lower-cost products and decreasing emissions. Additionally, the presently disclosed vapor phase infiltration reactor systems and methods can be beneficial as it can minimize thermal loss and allow for increased control of the temperature, pressure, and residence time within a reaction vessel.

FIG. 1 is a schematic view of reaction chamber 10, and it is understood that the design of chamber 10 may vary. In at least one embodiment, chamber 10 comprises an ultra-high vacuum rated vacuum chamber 12 attached to a high vacuum pump 14, a capacitance pressure gauge 16, and precursor bottle 18. In certain aspects of the disclosure, the reaction chamber 10 may further comprise electric heater 20 used to maintain a constant external wall temperature of vacuum chamber 12. In certain aspects of the disclosure, a software sequencer (not shown) is used to actuate diaphragm valve 26 which controls the release of the precursors into the vacuum chamber 12. In certain aspects of the disclosure, rotary spindles 28 are incorporated into vacuum chamber 10 to allow for the mounting of fabric bolts (not shown) and to maximize precursor penetration rates. In certain aspects of the disclosure, an independently heated stage (not shown) is incorporated into chamber 10 so that sample materials, such as substrates, can be exposed to varying temperatures. Substrate 34 is loaded into vacuum chamber 12 in a configuration that is conventional in the state of the art. In certain aspects of the disclosure, substrate 34 may include a bulk quantity of material in the form of a block or sheet attached to rotary spindles 28. In certain aspects of the disclosure, a chemical vapor infiltration reaction chamber comprises vacuum chamber 12; vacuum chamber 12 attached to vacuum pump 14 for controlling pressure inside the vacuum chamber; a substrate 34 loaded inside the vacuum chamber 12; and precursor bottles 18 positioned to dose precursors directly into vacuum chamber 12.

Figure 2:
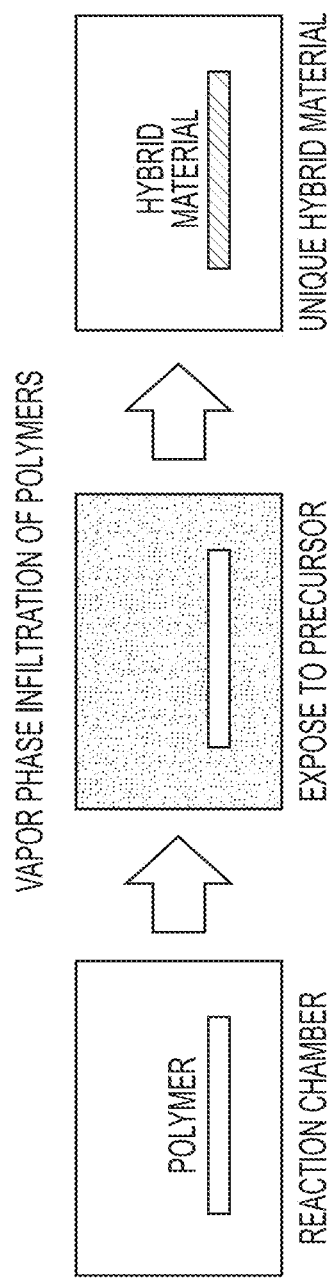
FIG. 2 is a diagram showing how a reaction chamber of a chemical vapor infiltration installation is filled, in accordance with an embodiment of the present disclosure.

As shown in FIG. 2, in certain aspects of the disclosure, the substrate is dosed with a precursor to form a hybrid material. In certain aspects of the disclosure, the method of chemically modifying polymeric materials includes dosing a substrate with a precursor to form a hybrid material. In another aspect of the disclosure, the process includes: (1) sorption of a gas phase precursor into a substrate, (2) transport of the precursor within the bulk substrate, and (3) entrapment of the precursor within the substrate. In certain aspects of the present disclosure, the method of chemically modifying polymeric materials includes loading a substrate into the vacuum chamber 12 of the VPI chamber 10; pumping chamber pressure down to high vacuum levels with high vacuum pump 14; dosing a precursor into the chamber by opening diaphragm valve 26; creating a static precursor atmosphere inside the chamber by closing diaphragm valve 26; allowing the substrate to rest in the static precursor atmosphere for a given time; and extracting the precursor from the chamber. In certain aspects of the disclosure, the vacuum chamber is further to atmospheric pressure and the substrate removed. In certain aspects of the disclosure, the precursor is dosed directly into the chamber.

In certain aspects of the disclosure, suitable chamber pressure during the pumping step is $1\times10^6$ mTorr to 20 mTorr. In certain aspects of the disclosure, suitable chamber pressure during the pumping step is $1\times10^{-4}$ mTorr to 10 mTorr. In certain aspects of the disclosure, suitable chamber pressure during the pumping step is $1\times10^{-2}$ mTorr to 5 mTorr. In certain aspects of the disclosure, suitable chamber pressure is $1\times10^{-6}$ mTorr or greater (e.g. $1\times10^{-4}$ mTorr, $1\times10^{-2}$ mTorr, 1 mTorr, 2 mTorr, 3, mTorr, 4 mTorr, 5 mTorr, 6 mTorr, 7 mTorr, 8 mTorr, 9 mTorr, 10 mTorr, 11 mTorr, 12 mTorr, 13 mTorr, 14 mTorr, 15 mTorr, 16 mTorr, 17 mTorr, 18 mTorr, 19 mTorr). In certain aspects of the disclosure, suitable chamber pressure is 20 mTorr or less (e.g. 19 mTorr, 18 mTorr, 17 mTorr, 16 mTorr, 15 mTorr, 14 mTorr, 13 mTorr, 12 mTorr, 11 mTorr, 10 mTorr, 9 mTorr, 8 mTorr, 7 mTorr, 6 mTorr, 5 mTorr, 4 mTorr, 3 mTorr, 2 mTorr, 1 mTorr, $1\times10^{-2}$ mTorr, $1\times10^{-4}$ mTorr).

In certain aspects of the disclosure, the substrate rests in the static precursor atmosphere from 1 second to 48 hours. In other aspects of the disclosure, the substrate rests from 10 minutes to 10 hours. In certain aspects of the disclosure, the substrate rests from 10 seconds to 1 hour. In some embodiments, the substrate rests for 1 second or greater (e.g., 5 seconds or greater, 15 seconds or greater, 30 seconds or greater, 1 minute or greater, 5 minutes or greater, 15 minutes or greater, 30 minutes or greater, 1 hour or greater, 2 hours or greater, 5 hours or greater, 10 hours or greater, 15 hours or greater, 20 hours or greater, 24 hours or greater, 30 hours or greater, 45 hours or greater). In some embodiments, the substrate rests for 48 hours or less (e.g., 45 hours or less, 30 hours or less, 24 hours or less, 20 hours or less, 15 hours or less, 10 hours or less, 5 hours or less, 2 hours or less, 1 hour or less, 30 minutes or less, 15 minutes or less, 5 minutes or less, 1 minute or less, 30 seconds or less, 15 seconds or less, 5 seconds or less).

In certain aspects of the disclosure, the sorption of precursor gas molecules into the substrate is dissolution into a polymeric material. However, precursor-polymer solubility is needed for successful vapor phase infiltration. Without solubility, the precursor molecule will not enter the polymer. This is a complex physiochemical process that is often simplified with classical continuum thermodynamics. In the case of pure dissolution, Henry's law is used:

$$C = S \cdot p.$$

Here, C, the concentration of a penetrant molecule in a polymer, depends upon the partial pressure (p) of the penetrant species and its solubility coefficient (S). This solubility coefficient scales exponentially with temperature (T) according to the van't Hoff equation:

$$S = S_0 \exp\left(-\frac{\Delta H_S}{kT}\right)$$

where $S_0$ is a scaling constant, k is Boltzmann's constant, and $\Delta H_S$ is the partial molar enthalpy of sorption. These equations are useful for experimentally evaluating the disclosed sorption processes. Equilibrium solubility coefficients can be measured gravimetrically (by mass) or nanometrically (by pressure) by exposing the sorbent to a constant pressure of precursor gas. An Arrhenius type plot of solubility coefficients at different temperatures can then be used to extract $\Delta H_S$. Gravimetric methods are routinely used in the art to experimentally study the solubility of metalorganic precursors in several polymers.

The polymeric material can be an organic based polymer. Organic based polymers suitable for use in the composites of the present disclosure can be homopolymers, copolymers, multicomponent polymers, or combinations thereof. Suitable organic polymers include halopolymers, such as fluoropolymers and fluorochloropolymers, polyimides, polyamides, polyalkylenes, such as polyethylene, polypropylene, and polybutylene, poly(phenylenediamine terephthalamide) filaments, modified cellulose derivatives, starch, polyesters, polymethacrylates, polyacrylates, polyvinyl alcohol, copolymers of vinyl alcohol with ethylenically unsaturated monomers, polyvinyl acetate, poly(alkylene oxides), vinyl chloride homopolymers and copolymers, terpolymers of ethylene with carbon monoxide and with an acrylic acid ester or vinyl monomer, polysiloxanes, polyfluoroalkylenes, poly(fluoroalkyl vinyl ethers), homopolymers and copolymers of halodioxoles and substituted dioxoles, polyvinylpyrrolidone, or combinations thereof. Halopolymers are organic polymers which contain halogenated groups, such as fluoroalkyl, difluoroalkyl, trifluoroalkyl, fluoroaryl, difluoroalkyl, trifluoroalkyl, perfluoroalkyl, perfluoroaryl chloroalkyl, dichloroalkyl, trichloroalkyl, chloroaryl, dichloroalkyl, trichloroalkyl, perchloroalkyl, perchloroaryl, chlorofluoroalkyl, chlorofluoroaryl, chlorodifluoroalkyl, and dichlorofluoroalkyl groups. Halopolymers include fluorohydrocarbon polymers, such as polyvinylidine fluoride (PVDF), polyvinylflouride (PVF), polychlorotetrafluoroethylene (PCTFE), polytetrafluoroethylene (PTFE) (including expanded PTFE ("ePTFE").

In certain aspects of the disclosure, the polymeric material can alternatively be an inorganic-organic hybrid polymer or blend of organic polymer and inorganic-organic hybrid polymer. Inorganic-organic hybrid polymers suitable for the practice of the present disclosure include those prepared by conventional methods for making organic-inorganic hybrid materials.

The polymer matrix can be of any form suitable for the use to which the substrate is to be put. For example, the polymer matrix can be an organic based polymer resin, powder, or particulate or, alternatively, an inorganic-organic hybrid polymer resin, powder, or particulate. Suitable particulate forms include sheets, fibers, or beads. As used herein, sheets are meant to include films, fibers are meant to include filaments, and beads are meant to include pellets. Beads have particle size of from 0.1 mm to 0.5 mm and powders have particle size of from 10 nm to 0.1 mm. In some embodiments, the bead particle size is 0.1 mm or greater (e.g. 0.2 mm or greater, 0.3 mm or greater, 0.4 mm or greater). In some embodiments, the bead particle size is 0.5 mm or less (e.g. 0.4 mm or less, 0.3 mm or less, 0.2 mm or less). In some embodiments, the bead particle size is 0.1 mm or greater (e.g. 0.2 mm or greater, 0.3 mm or greater, 0.4 mm or greater). In some embodiments, the bead particle size is 0.5 mm or less (e.g. 0.4 mm or less, 0.3 mm or less, 0.2 mm or less).

A wide variety of precursors can be used to diffuse various materials in accordance with certain aspects of the disclosure. By way of non-limiting example, suitable precursors include elemental Zn, elemental Cd, elemental S, elemental Se, ZnO, AlCl, $TiCl_4$, $TiO_2$, $TzCl_5$, $TzCl_5$, $Me_2AlCl$, trimethyl aluminum (TMA), titanium isopropoxide (TIP), diethyl zinc (DEZ), alkyls, tetrakisalkylamidos, cyclopentadienyls, and diketonates. By way of further non-limiting example, many oxygen or nitrogen sources can be used as a second precursor when depositing oxides or nitrides. For example, $O_2$, $H_2O$, $H_2O_2$, $O_3$, and aluminum alkoxides and other materials can be used as an oxygen providing second precursor. In some embodiments, the precursor is dosed into the chamber at 10 to 50 mL/min. In some embodiments, the precursor is dosed into the chamber at 15 to 35 mL/min. In some embodiments, the precursor is dosed into the chamber at 10 to 20 mL/min. In some embodiments, the precursor is antimicrobial or imparts antimicrobial properties. In some embodiments, the precursor is antifungal or imparts antifungal properties. In some embodiments, the precursor is hydrophobic or imparts hydrophobic properties. In some embodiments, the precursor is solvent resistant or imparts solvent resistance properties. In some embodiments, the precursor prevents yellowing or imparts properties which prevent yellowing.

Diffusion and reaction of molecular precursors within the polymer determines the fraction of material transformed. It would be readily apparent to those skilled in the art that the transport of gaseous species through polymer films is routinely subdivided into four primary categories: (1) viscous flow, (2) Knudsen diffusion, (3) molecular sieving, and (4) solution-diffusion. The first three methods are primarily driven by pressure gradients, while solution-diffusion is driven by chemical potential gradients. Once the gas molecule enters the polymer, it is referred to as a "penetrant" In viscous flow and Knudsen diffusion, penetrant molecules enter the polymer through macro-scale porosity, making these mechanisms of minimal importance for most VPI processes. Viscous flow occurs when the pore size is greater than the gas's mean free path (on the order of 0.1 mm or greater), resulting in gas flow similar to fluid flow through macro-scale tubes. As the pore radius shrinks below the size of the gas's mean free path, Knudsen diffusion becomes dominant. In the Knudsen diffusion regime, molecules move independently because molecule-molecule collisions are rare. Molecular sieving occurs when pore sizes approach the size of the gas molecule penetrant (a few nanometers). While molecular sieving may be important for some VPI processes, solution-diffusion is the most likely penetrant transport method. Solution-diffusion occurs in fully dense polymers and relies upon a combination of both gas molecule dissolution and diffusion. Unlike the other three transport mechanisms, solution-diffusion relies on physiochemical interactions between the diffusing molecules and the substrate.

The steady-state flux (J) of gas penetrant molecules across a polymer film of thickness (t) is described by Fick's 1st law:

$$J = -D\frac{(C_2 - C_1)}{t}$$

where D is the diffusivity of the penetrant, $(C_2-C_1)$ is the concentration gradient across the film, and t is the film's thickness. For a solution diffusion process, concentrations can be substituted with the equilibrium vapor pressures according to Henry's law (eqn (1)), giving:

$$J = -D\frac{S(p_2 - p_1)}{t}.$$

This equation suggests that a new proportionality constant can be defined to relate the diffusing flux to the pressure gradient for a solution-diffusion process. This new proportionality constant is known as the permeation coefficient or permeability (P) of the material:

$$P = D \cdot S$$

Accordingly, the permeability of a material—which is the combined sorption and diffusion properties for a given precursor-polymer couple—may be used to optimize the VPI process design.

Entrapment of the precursor molecule within the polymer matrix is necessary to complete the VPI process. The most direct method for precursor entrapment is the chemical reaction of penetrant molecules with polymer functional groups. However, other mechanisms, such as reaction with a secondary precursor (co-reactant) or physical entrapment, are also possible. In certain aspects of the disclosure, the method of chemically modifying polymeric materials further comprises dosing the polymeric material with a co-reactant to trap the metalorganic precursor within the polymeric material. In certain aspects of the disclosure, the method of chemically modifying polymeric materials repeatedly dosing the polymeric material with the metalorganic precursor and the co-reactant 2 to 20 times to grow the size of the inorganic phase and increase inorganic loading. In some embodiments, the repeated dosing is 2 times or greater (e.g., 3 times or greater, 4 times or greater, 5 times or greater, 6 times or greater, 7 times or greater, 8 times or greater, 9 times or greater, 10 times or greater, 11 times or greater, 12 times or greater, 13 times or greater, 14 times or greater, 15 times or greater, 16 times or greater, 17 times or greater, 18 times or greater, 19 times or greater). In some embodiments, the repeated dosing is 20 times or less (e.g., 19 times or less, 18 times or less, 17 times or less, 16 times or less, 15 times or less, 14 times or less, 13 times or less, 12 times or less, 11 times or less, 10 times or less, 9 times or less, 8 times or less, 7 times or less, 6 times or less, 5 times or less, 4 times or less, 3 times or less, 2.5 times or less). In some embodiments, the repeated dosing is from 2 to 20 times (e.g., from 2-5 times, from 2-10 times, from 5-10 times, from 10-15 times, from 15-20 times).

In some aspects, an organic species to the chamber to plasticize the polymeric material and accelerate diffusion of the precursor and/or co-reactant. Suitable organic species include toluene, acetone, methanol, ethanol, hexane, monomers of the polymer, or combinations thereof.

Figure 3A:
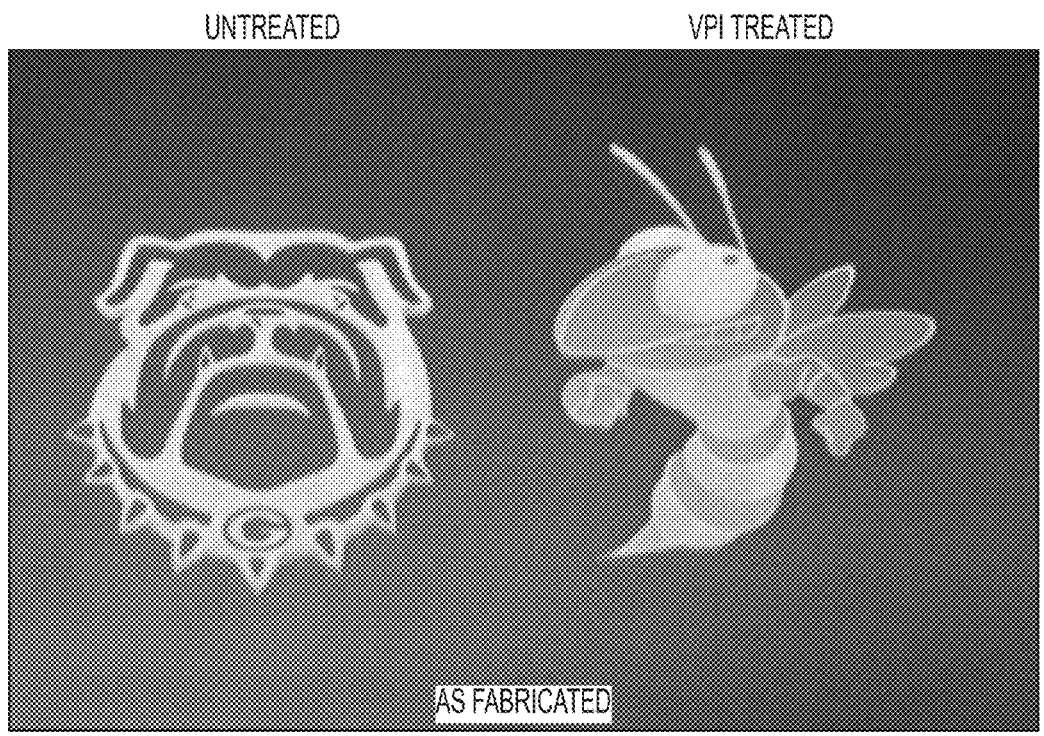
FIGS. 3A-3B is a set of photographs showing an implementation of the method of the disclosure wherein TMA is infiltrated into PMMA to make organic solvent resistant polymers, in accordance with an embodiment of the present disclosure.
Figure 3B:
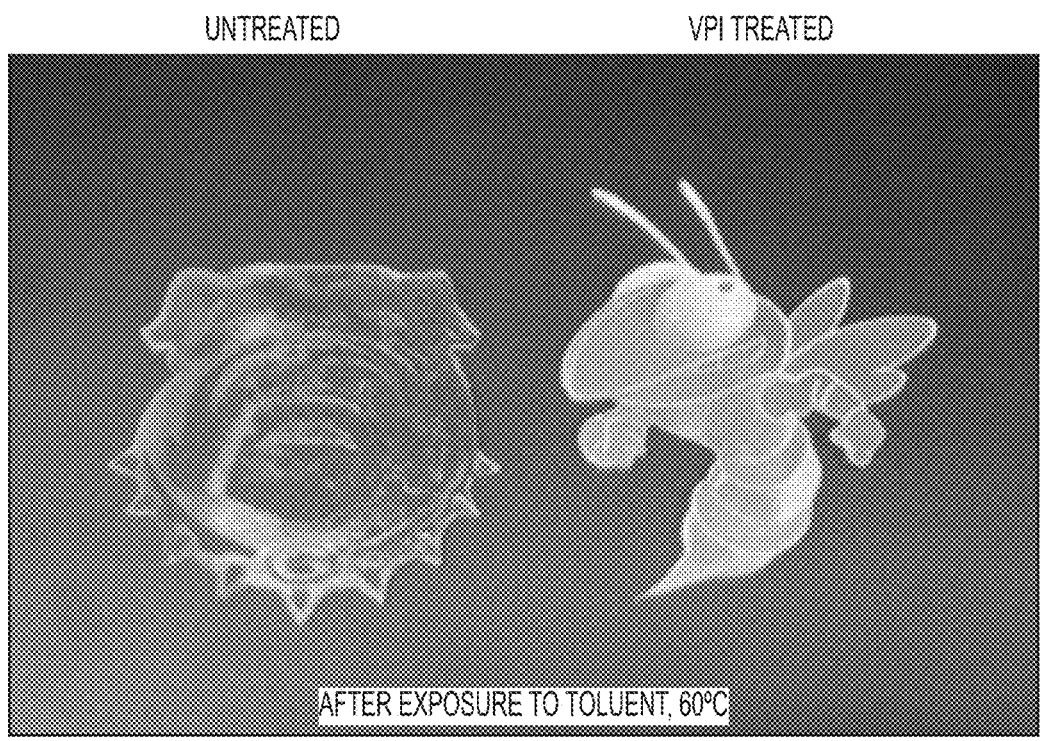

FIGS. 3A-3B show an implementation of the method of the disclosure, wherein TMA is infiltrated into PMMA to make organic solvent resistant polymers, in accordance with an embodiment of the present disclosure. Specifically, FIG. 3A shows two macroscale products, one untreated and the other VPI treated. FIG. 3B shows the same macroscale products after exposure to toluene, an organic solvent, at 60° C. The untreated is product is notably disintegrated and the VPI treated product is not.

Figure 4:
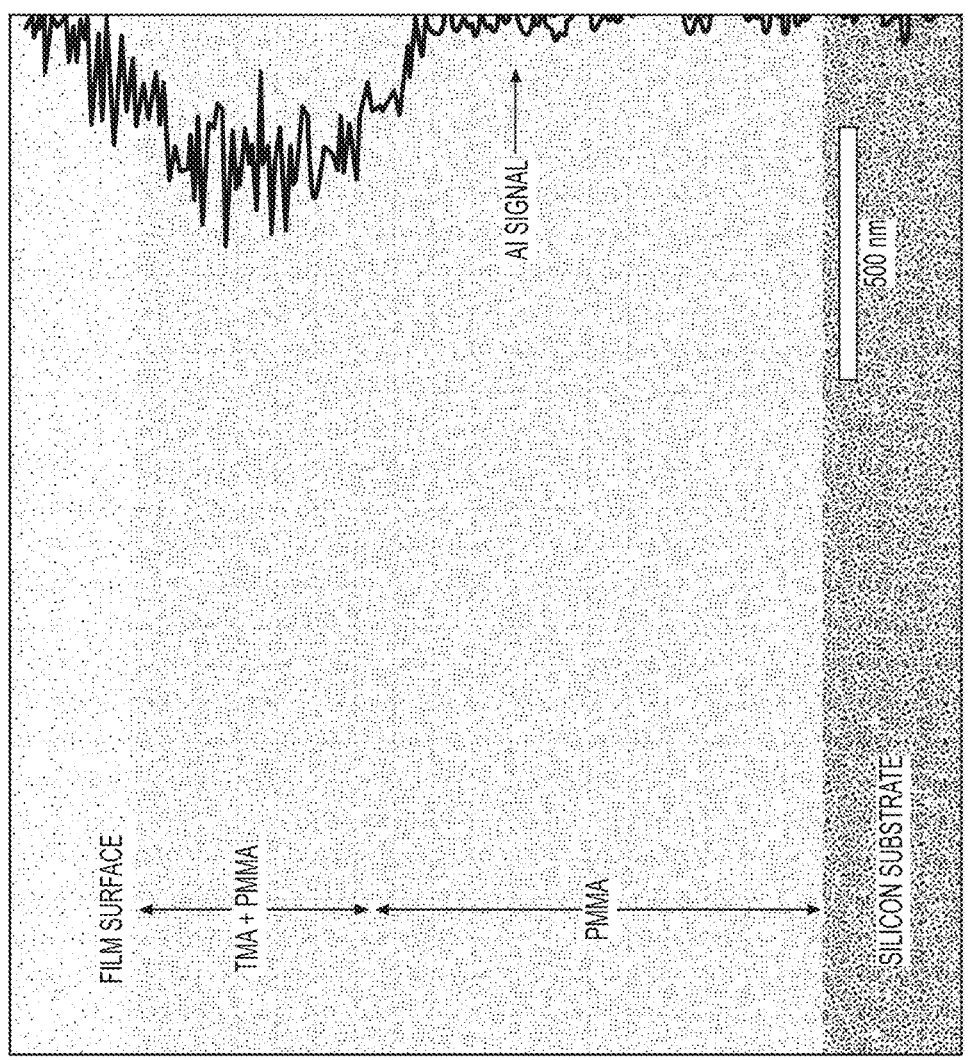
FIG. 4 is a diagram showing a reaction between a substrate and a precursor to form a resulting hybrid material, in accordance with an embodiment of the present disclosure.

FIG. 4 tracks a reaction between a substrate and a precursor forming a hybrid material. Specifically, it tracks the reactivity of a VPI modified PMMA film. Here trimethyl aluminum was exposed to PMMA for a set amount of time to partially infiltrate the film to a predesigned depth of interest to the practitioner. The image is an electron micrograph with an elemental map overlayed collected with energy dispersive x-ray spectroscopy. This image demonstrates the ability to use time, temperature, and partial pressure to control the amount of transformation in a material.

In accordance with same, at least four physiochemical features of the gaseous precursor molecules and/or polymer matrix are identified as contributors to the sorption, diffusion, and entrapment kinetics that occur during VPI processing: (1) size and shape of the precursor penetrant molecule, (2) free volume of the polymer, (3) process temperature, and (4) reactivity between precursor and polymer functional groups.

Molecular size and shape likely affect dissolution and diffusion of penetrant molecules in polymers. For example, atoms pack less densely in amorphous materials than crystalline materials.

In certain aspects of the disclosure, the materials that make up the polymer matrix contain natural free volume. The term "free volume," as used herein, relates to the vacant sites which are present in amorphous regions of a polymer matrix and into which organic or inorganic molecules can diffuse. The free volume can be exploited in accordance with the present disclosure as regions into which inorganic or organic materials can be introduced, such as by diffusion, and subsequently assembled into nanoparticles or other types of macromolecular networks or stabilized through interaction with the polymer matrix's functionality. These free volumes generally form during the curing process, such as upon evaporation of the solvent in which the polymer was formed, but the present disclosure is not intended to be limited by the mechanism by which the free volume comes to exist in the polymer matrix. In some embodiments, a cross-linker is not needed. In some embodiments, curing is not needed.

VPI is also controlled by the processing temperature. Both reaction rates and diffusion rates into the polymeric substrates may depend on temperature. Indeed, in certain aspects of the disclosure, the method of chemically modifying polymeric materials further comprises cycling the temperature in the chamber to prevent out-diffusion of the precursor and/or co-reactant. Furthermore, many polymeric materials decompose or undergo significant structural transition at moderate temperatures of from 60° C. to 300° C. Tuning the processing temperature while maintaining the desired structure of the polymer or any additives is an additional optimization parameter than can be adjusted for various end applications. Moreover, as process temperature increases, reaction rates increase and gaseous precursors become more likely to react near the polymer's surface. This reacted surface layer can act as a barrier to subsequent diffusion. As temperature increases, the carbonyl groups become more reactive towards TMA and trap more precursors at the surface, preventing any significant subsurface reaction. At lower VPI process temperatures (about 30° C.), mass gain is greater because reaction rates are slower and precursors are given the opportunity to permeate the polymer matrix.

In certain aspects of the disclosure, the VPI process is optimized when the precursor-polymer couple is moderately reactive. In certain aspects of the disclosure, many metalorganic precursors have been found to be moderately reactive with polymers containing carbonyl or amide functional groups. For the case of moderate reactivity, penetrant molecules can diffuse substantially into the polymer prior to becoming entrapped via chemical reaction. Another route to achieving this moderate reactivity is via the use of polymer blends or copolymers with mixtures of highly reactive and nonreactive monomer units. Upon chemical reaction, the inorganic moiety is permanently bound to the polymer and cannot be removed. This type of VPI process may be site-limited and self-terminating. However, these self-terminating reactions are not restricted to surface sites. Bulk diffusion to these sites is necessary to reach site saturation. Other considerations, including cross-linking and steric hindrance may also affect saturation concentrations.

Precursor-polymer couples that are unreactive towards one another can be difficult to entrap (e.g., the case of most metalorganic precursors with purely hydrocarbon polymers like polyethylene or polypropylene). While precursor penetrants may be able to sorb and diffuse throughout the polymer, physical binding mechanisms may be insufficient to retain these molecules upon removal of the precursors' overpressure and subsequent purge steps. In some aspects of the disclosure, to compel VPI into unreactive polymers is to introduce a second precursor (co-reactant) that reacts with the initial penetrant and drives entrapment. For these cases, site-saturation is no longer meaningful. No fixed number of reaction sites exists within the unreactive polymer, and deposition becomes completely reliant on the relative kinetics of precursor and co-reactant in-diffusion/out-diffusion and reaction rates. Surprisingly, with VPI, volatile precursor chemistries, such as trimethylaluminum, dietheylzinc, and titanium isorpropoxide, that may not be reactive for chemical vapor deposition processes at certain temperatures, could be utilized and entrapped within the polymer to create a stable hybrid material.

Figure 5:
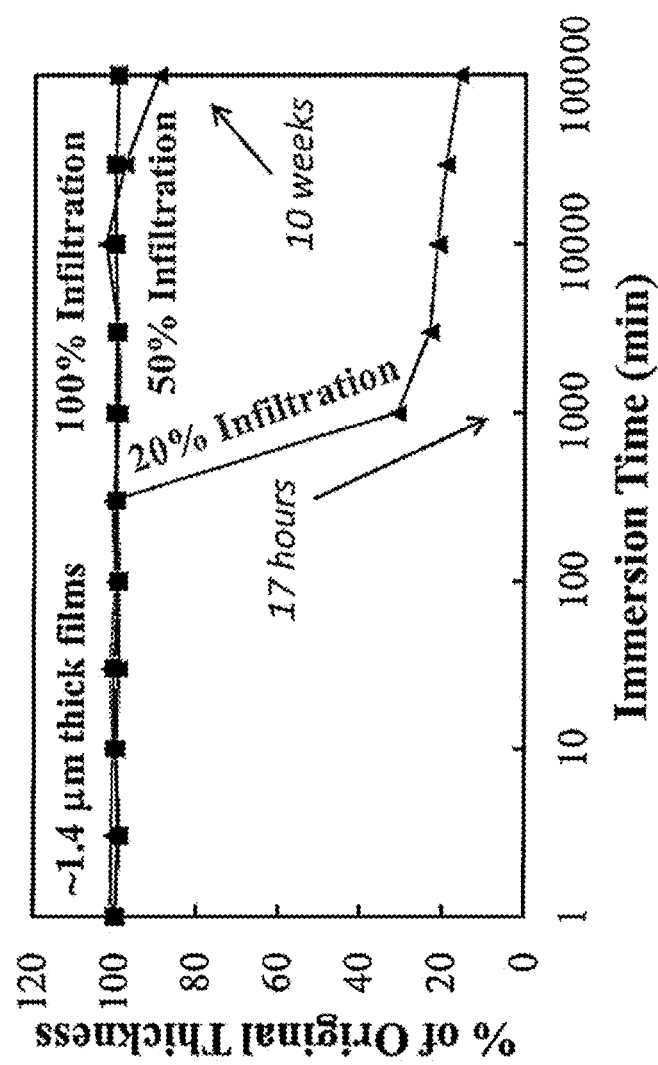
FIG. 5 is a diagram demonstrating chemical stability of certain VPI-modified materials.

FIG. 5 shows a 1.4 micron film of TMA VPI-modified PMMA on silicon that was immersed in toluene. Fully infiltrated films (100%) are chemically stable against dissolution indefinitely (2 months+). Partially infiltrated films can provide good chemical stability as well. Here, if infiltration thickness was about 0.7 microns, there is good stability for at least two months in toluene. For 20% infiltration there is good stability for at least 12 hours.

EXAMPLES

The following Examples are only illustrative and are not intended to limit the scope of the disclosure in any manner. It will be readily seen by one of ordinary skill in the art that the present disclosure fulfills all of the objectives set forth above. It is therefore intended that the protection granted herein be limited only by the definition contained in the appended claims and equivalents thereof.

Example 1: Preparation of a Hybrid Material Using the VPI Process

Poly-(ethylene terephthalate) (PET) is loaded into a vacuum chamber. The chamber is then pumped down to high-vacuum levels, approximately 10 mTorr. Active pumping is stopped. A software sequencer is then used to open and close a valve which doses a DEZ precursor into the chamber. The PET then rests in the DEZ atmosphere for a given time of 10 seconds and 6 hours. The residual DEZ is then pumped out and the chamber is vented to atmospheric pressure. The resulting DEZ-PET hybrid material can be used for antimicrobial treatments, such as antimicrobial garments, particularly in healthcare settings, antimicrobial garments for athletic application, antimicrobial protective gear, such as gloves, antimicrobial treatments for wooden construction that avoid the use of noxious chemicals like formaldehyde, and antimicrobial wound dressings that do not require pharmaceuticals, to name a few.

Example 2: Preparation of a Hybrid Material Using the VPI Process

Polycarbonate is loaded into a vacuum chamber. The chamber is then pumped down to high-vacuum levels, approximately 10 mTorr. Active pumping is stopped. A software sequencer is then used to open and close a valve which doses a ZnO or $TiO_2$ precursor into the chamber. The polycarbonate then rests in the ZnO or $TiO_2$ atmosphere for a given time of 10 seconds and 6 hours. The residual ZnO or $TiO_2$ is then pumped out and the chamber is vented to atmospheric pressure. The resulting ZnO-polycarbonate or $TiO_2$-polycarbonate hybrid material can be used, for example, for preventing yellowing in polycarbonate windows exposed to sunlight, or preventing degradation in outdoor lighting fixtures.

Example 3: Preparation of a Hybrid Material Using the VPI Process

Cellulose is loaded into a vacuum chamber. The chamber is then pumped down to high-vacuum levels, approximately 10 mTorr. Active pumping is stopped. A software sequencer is then used to open and close a valve which doses a TMA precursor into the chamber. The cellulose then rests in the TMA atmosphere for a given time of 1 second and 1 hour. The residual TMA is then pumped out and the chamber is vented to atmospheric pressure. The resulting TMA-cellulose hybrid material that is hydrophobic. The hydrophobic material may be used, for example, for water-resistant cardboard for shipping and transport, water stable paper for work orders, packing slips, or notebooks, non-water absorbing cotton fabric for application in athletic gear, fashion clothing, protective garments, and non-absorbent fabrics for upholstery or carpeting applications, to name a few.

Example 4: Preparation of a Hybrid Material Using the VPI Process

A carboxylate-containing polymer is loaded into a vacuum chamber. The chamber is then pumped down to high-vacuum levels, approximately 10 mTorr. Active pumping is stopped. A software sequencer is then used to open and close a valve which doses a TMA precursor into the chamber. The carboxylate-containing polymer then rests in the TMA atmosphere for a given time of 10 seconds and 12 hours. The residual TMA is then pumped out and the chamber is vented to atmospheric pressure. The resulting TMA-carboxylate hybrid material can be used, for example, for single-material chemically resistant protective gear, particularly safety goggles, transparent chemical-handling equipment and containers, and permanent curing of acrylic parts, to name a few.

Example 5: Preparation of a Hybrid Material Using the VPI Process

A poly(methyl methacrylate) plastic (PMMA) polymer is loaded into a vacuum chamber. The chamber is then pumped down to high-vacuum levels, approximately 10 mTorr. Active pumping is stopped. A software sequencer is then used to open and close a valve which doses a TMA precursor into the chamber. The PMMA polymer then rests in the TMA atmosphere for a given time of 1 second and one hour. The residual TMA is then pumped out and the chamber is vented to atmospheric pressure. The resulting TMA-PMMA hybrid material can be used, for example, for solvent resistance to toluene.

What is claimed is:

1. A method comprising:
   loading a substrate into a vacuum chamber of a chemical vapor infiltration reaction apparatus, the vacuum chamber having a first end and a second end with a high vacuum pump located proximate said second end;
   pumping the vacuum chamber to a pressure of from 8 mTorr to 12 mTorr with said vacuum pump;
   dosing the substrate with a metalorganic precursor by allowing the metalorganic precursor to flow inside the chamber;
   dosing the substrate material with a co-reactant to trap the metalorganic precursor within the substrate material;
   creating a static precursor atmosphere inside the chamber;
   allowing the substrate to rest in the static precursor atmosphere from 30 seconds to 1 day to form a chemically modified substrate; and
   extracting the chemically modified substrate from the vacuum chamber.

2. The method of claim 1, further comprising:
   extracting residual precursor from the chamber; and
   venting the vacuum chamber to atmospheric pressure.

3. The method of claim 1, wherein the substrate comprises an organic, polymeric material.

4. The method of claim 3, wherein the organic, polymeric material is selected from a group consisting of poly(methyl methacrylate) (PET), poly-(ethylene terephthalate) (PMMA), polycarbonate, cellulose, carboxylate-containing polymers, and combinations thereof.

5. The method of claim 1, wherein the precursor comprises a vapor phase metalorganic precursor.

6. The method of claim 5, wherein the metalorganic precursor is selected from a group consisting of titanium tetrachloride, zirconium tetrachloride, zinc chloride, aluminum trichloride, silane, tungsten hexafluoride, molybdenum fluoride, diethyl zinc, tetraethylorthosilicate, trim ethyl aluminum, titanium isopropoxide, dimethylchloro aluminum, methyldichloro aluminum, or other metal alkyls, metal tetrakisalkylamidos, metal cyclopentadienyls, metal diketonates, and combinations thereof.

7. The method of claim 1, wherein the chamber is pumped to a pressure of from 9 to 11 mTorr with the vacuum pump.

8. The method of claim 1, wherein the substrate rests in the static precursor atmosphere for about one hour.

9. The method of claim 1, wherein the extracted, chemically-modified substrate is a hybrid of the precursor and the loaded substrate.

10. A method comprising:
    loading a polymeric material into a vacuum chamber of a chemical vapor infiltration apparatus, the vacuum chamber having a first end and a second end with a high vacuum pump located proximate said second end;
    pumping the vacuum chamber to a pressure of from 8 mTorr to 12 mTorr with said vacuum pump;
    dosing the polymeric material with a metalorganic precursor by allowing the metalorganic precursor to flow inside the chamber;
    dosing the polymeric material with a co-reactant to trap the metalorganic precursor within the polymeric material;
    creating a static precursor atmosphere inside the chamber;
    allowing the polymeric material to rest in the static precursor atmosphere from 30 seconds to 1 day to form a chemically modified polymeric material; and
    extracting a chemically modified polymeric material from the chamber.

11. The method of claim 10, further comprising repeatedly dosing the polymeric material with the metalorganic precursor and the co-reactant from 2 to 20 times to grow the size of the inorganic phase and increase inorganic loading.

12. The method of claim 10, further comprising adding an organic species to the chamber to plasticize the polymeric material and accelerate diffusion of the precursor and/or co-reactant.

13. The method of claim 10, further comprising cycling the temperature in the chamber to prevent out-diffusion of the precursor and/or co-reactant.

14. The method of claim 10, wherein the extracted, chemically modified polymeric material has antimicrobial properties.

* * * * *